United States Patent [19]

Strickland

[11] 4,082,257
[45] Apr. 4, 1978

[54] SURGERY TABLE

[76] Inventor: James W. Strickland, 6969 Warwick Rd., Indianapolis, Ind. 46220

[21] Appl. No.: 785,406

[22] Filed: Apr. 7, 1977

[51] Int. Cl.² .......................................... A61G 13/00
[52] U.S. Cl. .................................................. 269/328
[58] Field of Search ................ 269/322, 327, 328, 15; 119/103

[56] References Cited

U.S. PATENT DOCUMENTS

| | | | |
|---|---|---|---|
| 2,832,313 | 4/1958 | Toepel | 119/103 |
| 2,945,731 | 7/1960 | Tutrone | 260/327 |
| 3,358,141 | 12/1967 | Hoffmann et al. | 269/328 |
| 3,779,211 | 12/1973 | Etes | 269/327 |

*Primary Examiner*—Robert C. Watson

*Attorney, Agent, or Firm*—Woodard, Weikart, Emhardt & Naughton

[57] ABSTRACT

A surgery table for use when performing a surgical procedure on the hand and including a support platform, a drain pan, a flexible tube, means for securing the hand to the support platform, and means for holding in position portions of the hand so that the portions do not interfere with performance of the surgical procedure. The support platform has a top surface that has openings therein for drainage of fluid from the top surface. The drain pan has a lip around its perimeter and a support surface upon which the support platform rests. The lip extends above the support surface of the drain pan thereby forming a reservoir capable of collecting fluid which drains through the openings from the top surface of the support platform. There is an aperture in the lip to which the flexible tube is connected for draining fluid from the reservoir.

11 Claims, 10 Drawing Figures

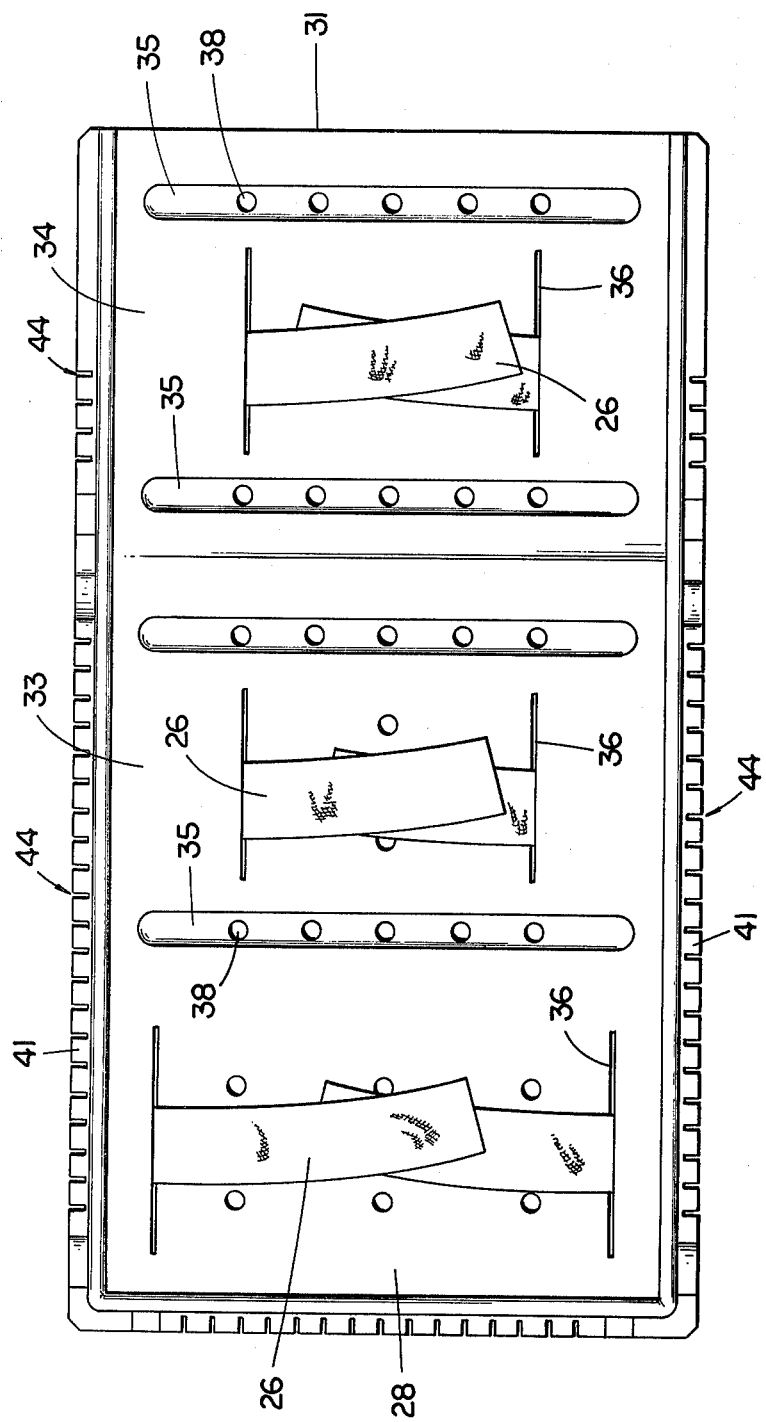
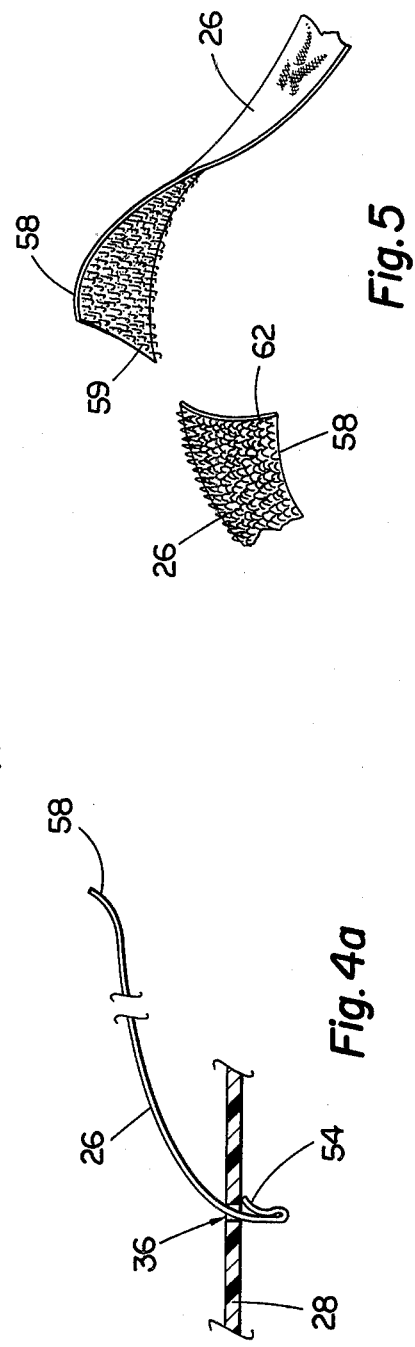
Fig. 4
Fig. 4a
Fig. 5

SURGERY TABLE

BACKGROUND OF THE INVENTION

1. Field of the Invention

This invention relates in general to medical devices, and more particularly to surgical tables.

2. Description of the Prior Art

Surgical tables associated with operations on human beings and for disecting animals have been therefore known in the art. Such tablets may have a variety of configurations, as well as features, and can accommodate either the entire patient or a portion of the anatomy.

One feature common to many such surgical tables is a means for draining fluid from the operating surface so that the fluid does not collect and interfere with the surgical procedure. The inventions of Ferguson, U.S. Pat. No. 1,822,206; Sweat, U.S. Pat. No. 2,460,857; and Tutrone, U.S. Pat. No. 2,945,731; disclose as one feature a means for drainage of fluid which consists of an opening in the top surface of the operating table through which fluids pass. In each of the devices, a container is placed beneath the table in order to collect the fluids. These devices may be suitable in situations where there is room to locate a container beneath the table or where a fixed point for drainage is acceptable. However, one disadvantage is that no flexibility is provided for the location of the point of drainage.

Another feature present on some of the prior art devices is a means for securing a portion of the anatomy to the operating surface. Landy, U.S. Pat. No. 3,286,694, and Creelman, U.S. Pat. No. Re. 24,377, disclose fairly complicated apparata for securing the anatomy. Landy, for use with animals, and Creelman, for use on infants, both involve the use of a table which is contoured to generally conform to the body of the animal or infant. Consequently, these devices have fixed positions for their securing means. The disadvantage is that variations in size of the animal or infant cannot be accommodated. Furthermore, the position of the anatomy cannot be easily shifted as might be desired during a surgical procedure. Hakstian, U.S. Pat. No. 3,746,332, and Etes, U.S. Pat. No. 3,779,211, disclose a means for securing the subject to the top surface of the operating table which avoids the rigid positioning of Landy and Creelman. Hakstian and Etes employ the use of elastic cord which is secured to each side of the table and spans the top surface of the operating table. Although the elastic cord concept allows greater flexibility in positioning, it does not permit variations in tension which might be desirable depending upon the size of the subject or portion of the anatomy.

A final feature of at least one operating table is a chain and hook device which allows pieces of flesh to be pierced by the hooks and then positioned by securing the chain to one side of the table. Sweat discloses such a device in which the chain is a ball chain design.

SUMMARY OF THE INVENTION

One embodiment of the present invention is a surgery table for use in performing a surgical procedure on a portion of the anatomy. The table comprises a support platform, a drain pan, a flexible tube, means for securing a portion of the anatomy to the support platform, and means for holding in position pieces of the anatomy so that the pieces do not interfere with performance of the surgical procedure. The support platform has a top surface, a base and sides extending between the top surface and the base. The platform has at least one opening for drainage of fluid from the top surface. The drain pan has a support surface upon which the support platform rests. The pan has a lip around its perimeter which extends above the support surface and thereby forms a reservoir capable of collecting fluid which drains through the opening from the top surface of the support platform. The lip has an aperture therein to which one end of the flexible tube is connected for draining fluid from the reservoir to a remote location.

Alternatives to the above embodiment are possible within the scope of this invention. One such alternative involves not limiting the drainage means to a flexible tube and using as the first means, a flexible, elongated strap secured to the top surface and means for securing the ends of the strap together.

It is an object of this invention to provide an improved surgery table which has means to permit drainage of fluid from the operating surface and to route the drainage to a selectable, remote location.

It is also an object of this invention to provide an improved surgery table which has means for securing the portions of anatomy to the table whereby the position of the portion can be easily changed during the surgical procedure and the tension on the portion of anatomy can be adjusted.

Related objects and advantages of the present invention will be apparent from the following description.

BRIEF DESCRIPTION OF THE DRAWINGS

FIG. 4 is a plan view of a support platform forming a part of the apparatus of FIG. 1.

FIG. 5 is a detailed view of the ends of a securing strap forming a part of the apparatus of FIG. 1.

DESCRIPTION OF THE PREFERRED EMBODIMENT

Figure 1:
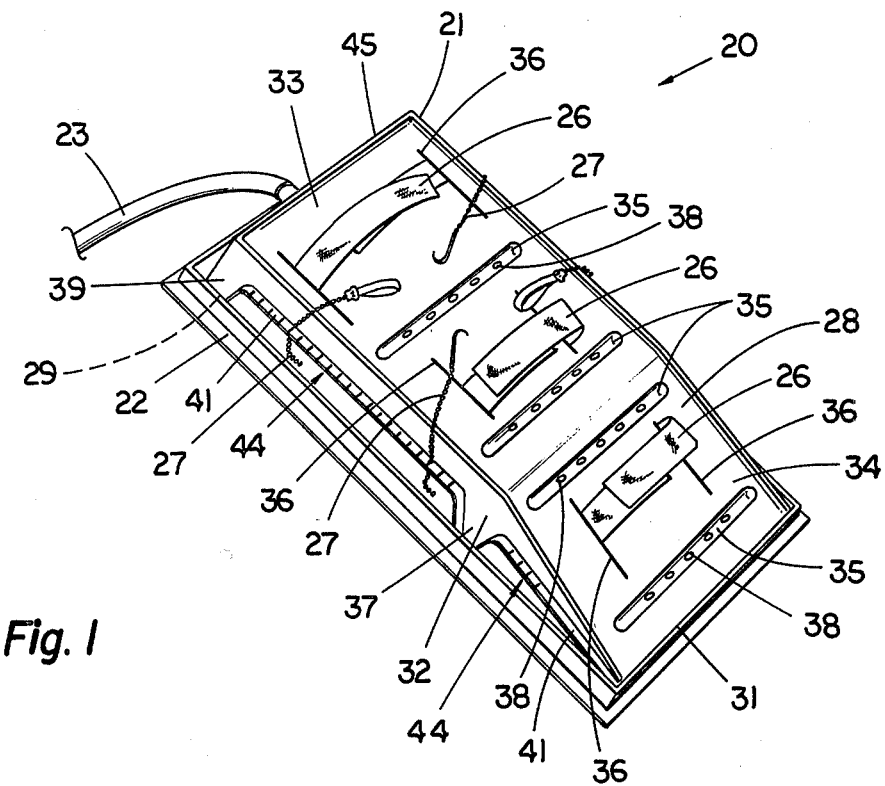
FIG. 1 is a perspective view of the surgery apparatus of the invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to the drawings, FIG. 1 is a perspective view of a surgery table 20 which includes support platform 21, drain pan 22, flexible tube 23, flexible securing straps 26 and ball chain retractors 27. Support platform 21 is generally rectangular in shape and has a top surface 28, base 29 and three sides 32 extending between top surface 28 and base 29. Top surface 28 consists of two generally-flat portions 33 and 34. Portion 33 is parallel to the surface on which the surgery table 20 is placed. Portion 34 is inclined downwardly from portion 33 to lower edge 31 which is adjacent to drain pan 22. Top surface 28 has a series of grooves 35 in both portions 33, 34 and in the bottom of each groove 35 there are a plurality of spaced openings 38. Top surface 28 has three pairs of longitudinal slots 36 which receive securing straps 26.

Figure 8:
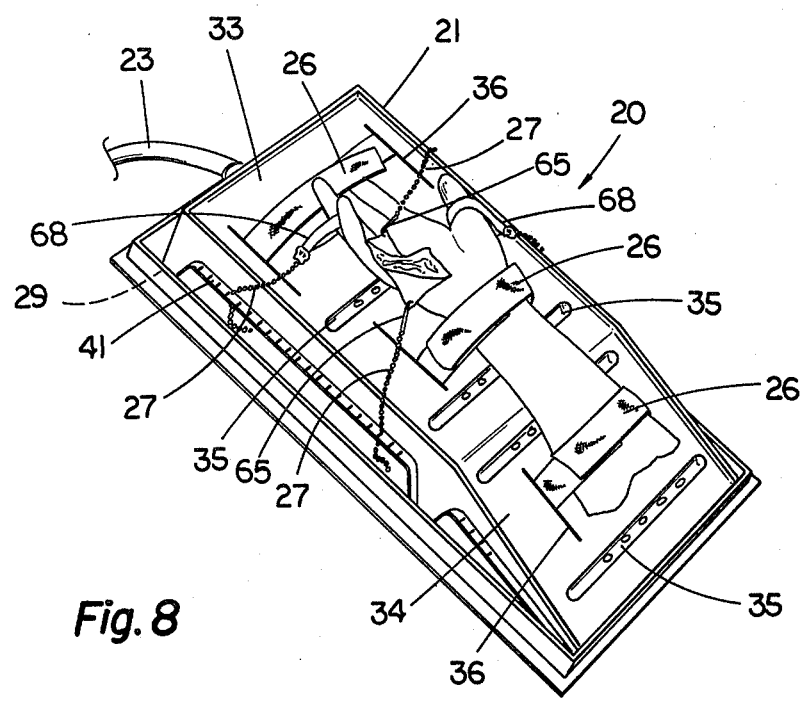
FIG. 8 is a perspective view of the FIG. 1 device showing a portion of anatomy secured to the top surface.
Figure 7:
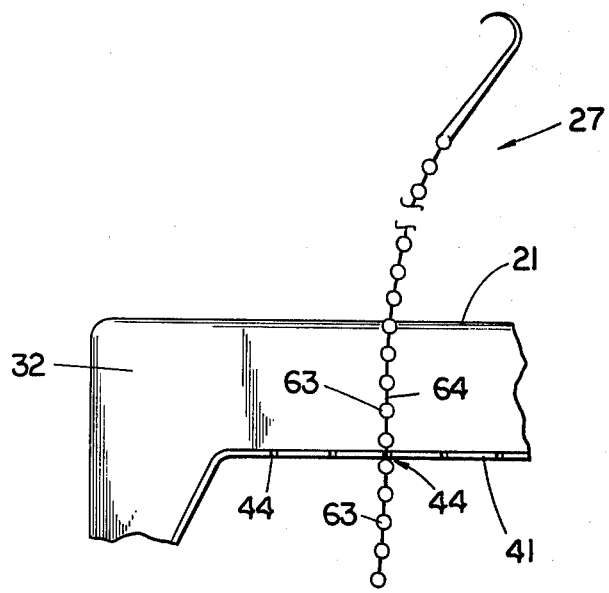
FIG. 7 is a detailed side view of the ball chain and hook apparatus of FIG. 6a secured to the FIG. 3 support platform.

The sides 32 are shaped in such a way that they form two pairs of legs 37, 39 which are spaced around support platform 21. Legs 39 are at the two corners of portion 33, while legs 37 are located adjacent to the point where portion 33 joins portion 34. Each of the three sides 32 of support platform 21 are formed with a flange 41 which extends the full length of each side 32. The flange 41 has a series of closely spaced notches 44 along the portions of the flange 41 which are between the legs 37, 39. Notches 44 receive and secure ball chain retractors 27 as shown in FIGS. 1, 7 and 8.

In this embodiment the ends 40 (se FIG. 3) of each leg 37, 39 collectively comprise base 29 of support platform 21. Edge 31 of platform 21, which can be thought of as a fourth side, is actually an edge common to top surface 28 as well as base 29.

Fluids are prevented from running off the edges of top surface 28 by means of ridge 45 which extends partially around the perimeter of surface 28. Ridge 45 does not extend along lower edge 31 of platform 21. Fluid present on top surface 28 will either collect in grooves 35 and drain through openings 38 or will run down inclined portion 34. Either way, the fluid will drain from top surface 28 and be collected in drain pan 22.

Figure 2:
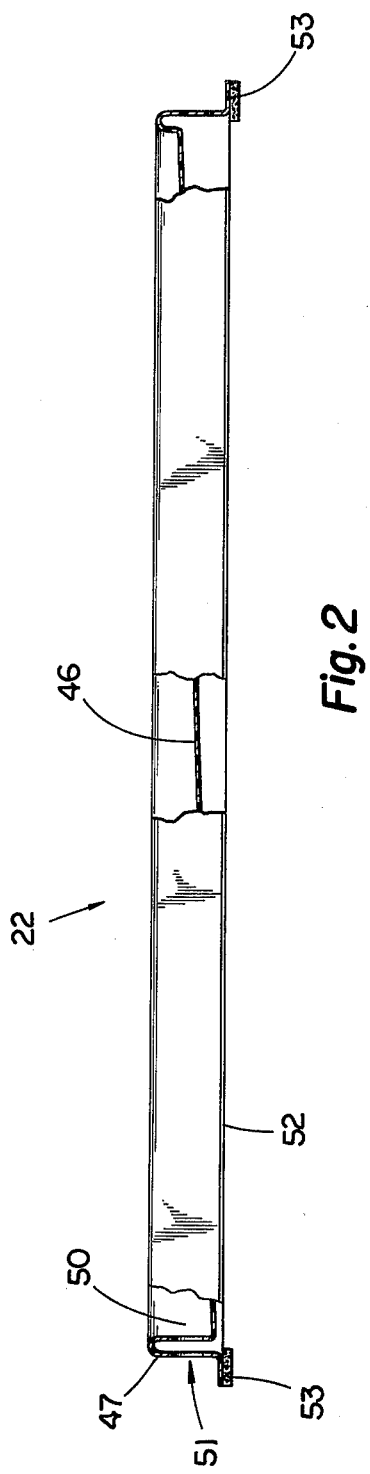
FIG. 2 is a fragmentary side view of a drain pan forming a part of the apparatus of FIG. 1.

FIG. 2 is a fragmentary side view of drain pan 22 showing support surface 46 upon which the base 29 of support platform 21 rests, and lip 47 around the perimeter of support surface 46. The lip 47 extends above support surface 46 and forms a reservoir 50 which is capable of collecting the fluid which drains from top surface 28 of support platform 21. At one end of pan 22, there is an aperture 51 in lip 47. Support surface 46 is an inclined surface which extends from the end of pan 22 opposite aperture 51 downwardly to a location slightly below aperture 51. The support surface 46 is also slanted downwardly from each side towards the center of surface 46, forming a V-shaped trough. This inclined configuration of support surface 46 allows all the fluid in reservoir 50 to be collected in the center of surface 46 and drain through aperture 51. Pan 22 has a generally-flat base 52 relative to inclined support surface 46. Attached to the base 52 are pads 53 of non-skid material. This non-skid material may be any suitable material which has a high coefficient of friction relative to a smooth hard surface such as steel or glass. These pads 53 prevent relative motion between surgery table 20 and the generally-flat surface on which table 20 is placed. For support surface 46 to function as described, the pads 53 on base 52 are placed on a generally-flat surface when the surgical table is to be used.

Figure 3:
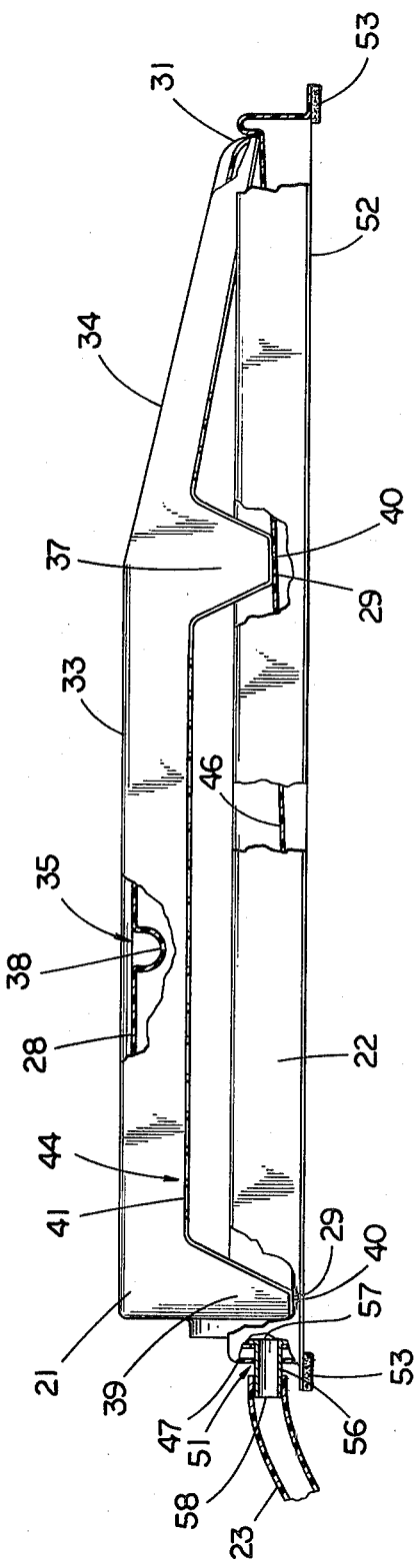
FIG. 3 is a fragmentary side view of the apparatus of FIG. 1.

FIG. 3 is a fragmentary side view of the surgery table 20 of FIG. 1 showing in detail the position of support platform 21 with respect to drain pan 22. Inclined support surface 46 is shown extending to a point just beneath aperture 51. In this embodiment, aperture 51 is fitted with a short rigid tube 56 which has a flange 57 at one end. Tube 56 is inserted through aperture 51 so that flange 57 rests up against the lip 47 of drain pan 22 and end 58 extends a short distance out from aperture 51. Flexible tube 23 is attached to rigid tube 56 by sliding tube 23 over end 58 of tube 56. The legs 37, 39 of support platform 21 are supported by inclined support surface 46. As surface 46 increases in elevation above the base 52 of drain pan 22, legs 37 must be shorter than legs 39 so that portion 33 of support platform 21 remains parallel to base 52 of drain pan 22.

The support platform 21 and drain pan 22 of surgery table 20 may be constructed of a material such as stainless steel which can be sterilized repeatedly for multiple usage. However, the preferred construction for table 20 is to be sterile and disposable. Thus, a suitable material would be high-impact polystyrene. One advantage of high-impact polystyrene is that it can provide a non-glare surface which is important when the surgical procedure is being performed under bright lights. The concept of non-glare, as the name implies, is descriptive of a low reflective surface which reflects back only a very low percentage of the light incident thereon. Flexible tube 23 can vary in diameter size as well as length and material. The preferred construction is for tube 23 to have approximately a ½ inch inside diameter and be of from 5 to 6 feet in length.

Referring to FIGS. 4 and 4a, the attachment of flexible securing straps 26 within longitudinal slots 36 of top surface 28 is shown in greater detail. Strap 26 may be either one continuous length or constructed into two pieces. The method of construction and attachment to platform 21 for such straps suggests that a two-piece construction is preferable. Each piece of the two-piece construction is folded and sewn together at end 54 thereby doubling the thickness of the strap 26 at end 54. When the strap 26 is inserted through slot 36, the width of slot 36 is not sufficient to allow the folded end 54 of strap 26 to pass through. The slots 36 are spaced on each side of top surface 28 so that the free ends 58 of strap 26 can surround portions of anatomy which are placed on surface 28. The free ends 58 of each strap 26 are secured together once the portion of anatomy is in position. Any number of securing means is possible for securing the free ends, but the preferred construction is shown by FIG. 5 in which tiny, hook-like projections 59 on one end of strap 26 interlock with loops 62 on the other end of strap 26. When slight pressure is applied pressing the respective ends together, the hook-like projections 59 and loops 62 interlock with one another. Straps 26 can thus be secured together as well as easily opened, and the tension around the portion of the anatomy being secured to top surface 28 can be easily adjusted.

Figure 6A:
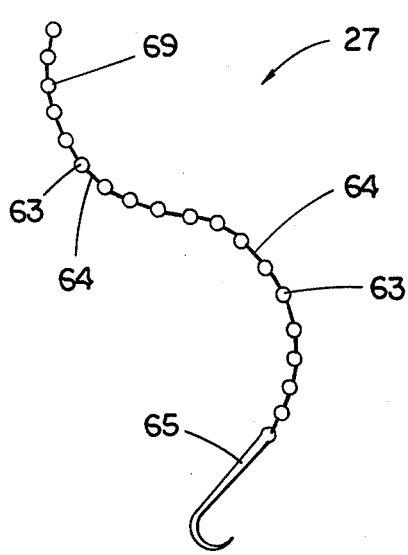
FIG. 6a is a detailed view of a ball chain and hook device.
Figure 6B:
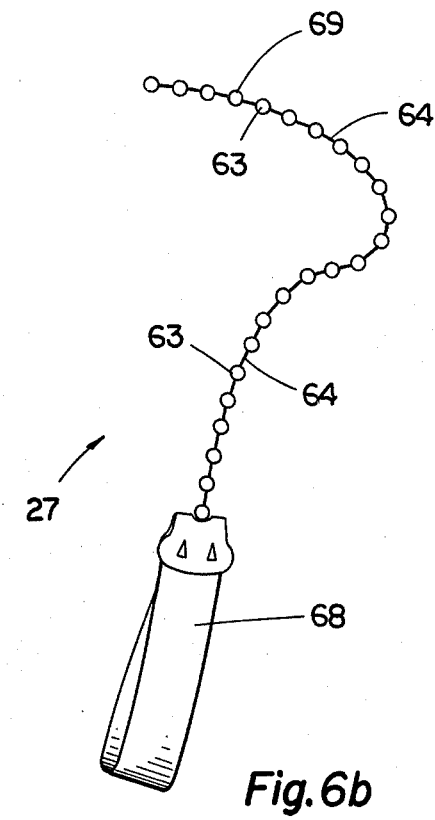
FIG. 6b is a detailed view of a ball chain and finger loop retractor device.

FIGS. 6a and 6b show two possible ball chain retractor configurations. Ball chains which are common with such items as keychains, consist of an alternating series of connected balls 63 and links 64. FIG. 6a shows a ball chain retractor 27 which employs a hook 65 attached to one end of the chain 69. One use for this type of retractor is to hook and pull back pieces of flesh on the sides of an incision. The ball chain retractor 27 configuration of FIG. 6b employs a finger loop retractor 68 which is attached to one end of the chain 69. This type of retractor is well suited for hand surgery where the fingers and thumb of the patient needed to be positioned in a certain manner.

FIG. 7 is a detailed view of the ball chain secured to one of the notches 44 in flange 41 of side 32 of support platform 21. By inserting one of the links 64 into one of the notches 44, a ball 63 is located on each side of notch 44. Since ball 63 is larger in diameter than the width of notch 44 and there is some tension pulling up on the retractor, the ball chain retractor 27 will be held in position. Depending upon which link 64 is inserted into which notch 44, the length and position of the ball chain retractors 27 can be varied.

FIG. 8 is a perspective view of the FIG. 1 surgery table 20 to which a hand, with a portion of the forearm, has been added in order to show the features of surgery table 20 when in use for a surgical procedure. Both types of ball chain retractors 27 are used, the hooks 65 for flesh and the finger loop retractors 68 for a finger and a thumb. The three flexible securing straps 26, each surround a differently-sized portion of the anatomy. Flexible tube 23 can be routed to any suitable remote container for disposing of fluid.

Although this table would normally find use in the sterile surroundings of a hospital operating room, it is equally suitable for emergency operations in any surrounding.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

I claim:

1. A surgery table for use when performing a surgical procedure on a portion of the anatomy which comprises:
   a support platform having a top surface, a base, and sides extending between said top surface and said base, said platform having at least one opening for drainage of fluid from the top surface;
   a drain pan having a support surface upon which said support platform rests, said pan having a lip around its perimeter, said lip extending above the support surface of said pan thereby forming a reservoir capable of collecting fluid which drains through said opening from the top surface of the support platform, said lip having an aperture therein;
   a flexible tube having one end connected to said aperture for draining fluid from the reservoir;
   first means for securing to the top surface of said support platform a portion of the anatomy; and
   second means for holding in position pieces of the anatomy so that the pieces do not interfere with performance of a surgical procedure.

2. The surgery table of claim 1 in which the sides of said support platform have a series of notches formed therein and said second means is a ball chain and retractor device which comprises an alternating series of connected balls and links forming a ball chain, and a retractor attached to one end of said chain, said ball chain being capable of being secured to said support platform by inserting one of said links into one of said notches.

3. The surgery table of claim 2 in which the support surface of the drain pan is an inclined surface extending downwardly to a location adjacent said aperture.

4. A surgery table for use when performing a surgical procedure on a portion of the anatomy which comprises:
   a support platform having a top surface, a base, and sides extending between said top surface and said base, said platform having a plurality of openings for drainage of fluid from the top surface, said base further having at least one pair of spaced apart slots;
   said top surface having a plurality of grooves, each of said plurality of grooves having at least one of said plurality of openings therethrough;
   a drain pan having a support surface upon which said support platform rests, said pan having a lip around its perimeter, said lip extending above the support surface of said pan thereby forming a reservoir capable of collecting fluid which drains through said opening from the top surface of the support platform;
   first means for draining said reservoir of fluid;
   a flexible, elongated strap passing through said slots, means for securing the ends of said strap together adjacent said top surface, said strap having a length sufficient to surround a portion of the anatomy when said portion is placed on the top surface of said platform; and
   second means for holding in position pieces of the anatomy so that said pieces do not interfere with performance of a surgical procedure on the anatomy.

5. The surgery table of claim 4 in which said means for securing the ends of said strap together is a plurality of hook-like projections at one end of said strap and a plurality of loops at the other end of said strap.

6. The surgery table of claim 4 in which said first means comprises a flexible tube and an aperture formed in said lip, said tube being connected to said aperture for draining fluid from the reservoir.

7. The surgery table of claim 5 in which the sides of said support platform have a series of closely spaced notches formed therein and said second means is a ball chain and retractor device which comprises an alternating series of connected balls and links forming a ball chain and a retractor attached to one end of said chain, said ball chain being capable of being secured to said support platform by inserting one of said links into one of said notches.

8. The surgery table of claim 7 in which the support surface of the drain pan is an inclined surface extending downwardly to a location below said aperture.

9. The surgery table of claim 8 in which said drain pan has a generally-flat base and has pads of material attached thereto having a high coefficient of friction relative to a smooth hard surface for preventing movement of said pan relative to a surface on which said pan is supported.

10. The surgery table of claim 9 in which said table is disposable and the top surface of said platform is a low reflective surface.

11. A surgery table for use when performing a surgical procedure on a portion of the anatomy which comprises:
   a support platform having a top surface, a base, and sides extending between said top surface and said base, said platform having at least one opening for drainage of fluid from the top surface, said base further having at least one pair of spaced apart slots;

a drain pan having a support surface upon which said support platform rests, said pan having a lip around its perimeter, said lip extending above the support surface of said pan thereby forming a reservoir capable of collecting fluid which drains through said opening from the top surface of the support platform;

first means for draining said reservoir of fluid;

a two-piece flexible strap member comprising a first piece having a free end passing through a first one of said spaced apart slots and a second end of a thickness greater than the width of said slot, a second piece having a free end passing through the other slot in a pair with said first one of said spaced apart slots and a second end of a thickness greater than the width of said other slot;

means for securing the free end of said first piece and the free end of said second piece together, said strap having a length sufficient to surround a portion of the anatomy when said portion is placed on the top surface of said platform; and second means for holding in position pieces of the anatomy so that said pieces do not interfere with performance of a surgical procedure on the anatomy.

* * * * *